United States Patent
Kutek

(10) Patent No.: US 10,449,379 B2
(45) Date of Patent: Oct. 22, 2019

(54) ENCODED STATUS INDICATOR FOR AUTOMATED EXTERNAL DEFIBRILLATORS

(71) Applicant: KONINKLIJKE PHILIPS N.V., Eindhoven (NL)

(72) Inventor: Lukasz Pawel Kutek, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 15/128,800

(22) PCT Filed: Feb. 4, 2015

(86) PCT No.: PCT/IB2015/050836
§ 371 (c)(1),
(2) Date: Sep. 23, 2016

(87) PCT Pub. No.: WO2015/145272
PCT Pub. Date: Oct. 1, 2015

(65) Prior Publication Data
US 2018/0214706 A1 Aug. 2, 2018

Related U.S. Application Data

(60) Provisional application No. 61/971,310, filed on Mar. 27, 2014.

(51) Int. Cl.
*A61N 1/00* (2006.01)
*A61N 1/39* (2006.01)
*A61N 1/04* (2006.01)

(52) U.S. Cl.
CPC ......... *A61N 1/3993* (2013.01); *A61N 1/3904* (2017.08); *A61N 1/3925* (2013.01); *A61N 1/046* (2013.01)

(58) Field of Classification Search
None
See application file for complete search history.

(56) References Cited

U.S. PATENT DOCUMENTS

| | | |
|---|---|---|
| 5,879,374 A | 3/1999 | Powers et al. |
| 5,904,707 A | 5/1999 | Ochs et al. |

(Continued)

FOREIGN PATENT DOCUMENTS

| | | |
|---|---|---|
| JP | 3156737 U | 12/2009 |
| JP | 2010098078 A | 4/2010 |

(Continued)

OTHER PUBLICATIONS

Borogovac et al: "Lights-Off Visible Light Communications" Proc. of 2nd IEEE Globecom 2011 Workshop on Optical Wireless Communications, Dec. 2011, pp. 1-14.

(Continued)

*Primary Examiner* — Amanda K Hulbert
*Assistant Examiner* — Elizabeth K So

(57) ABSTRACT

An automated external defibrillator ("AED") (10) employing a self-test circuit (11) and an encoded status indicator. The self-test circuit (11) automatically tests AED (10) and dependent upon the tests, generates both a base status signal (110) indicative of an operational readiness of AED (10) and a test status signal (120) indicative of self-test information of AED (10). The encoded status indicator concurrently visually indicates both the base status signal (110) and the test status signal (120) with the visual indication of the base status signal (110) being perceivable to a human eye and the visual indication of the test status signal (120) being unperceivable to the human eye. The encoded status indicator may employ a light source (14) for emitting a status light (20) and an encoder (13) to intensity modulate the status light (20) as emitted by the light source (14) as a function of an encoding (Continued)

Figure 1:
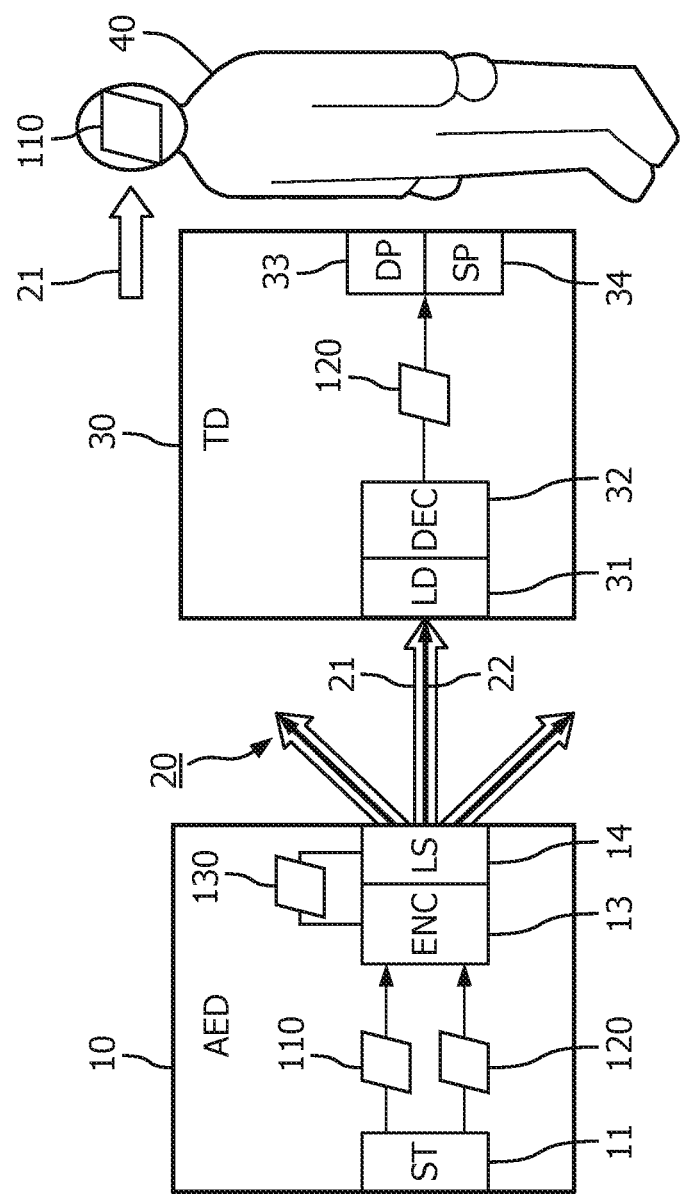

of the base status signal (110) and the test status signal (120) by the encoder (13).

17 Claims, 3 Drawing Sheets

(56) References Cited

U.S. PATENT DOCUMENTS

| | | | |
|---|---|---|---|
| 2006/0136000 A1* | 6/2006 | Bowers | A61N 1/3925 607/5 |
| 2011/0213433 A1 | 9/2011 | Vaisnys et al. | |

FOREIGN PATENT DOCUMENTS

| | | |
|---|---|---|
| JP | 2012171449 A | 9/2012 |
| JP | 2012215984 A | 11/2012 |
| WO | 2006102427 A2 | 9/2006 |
| WO | 2010007574 A1 | 1/2010 |
| WO | 2010007589 A1 | 1/2010 |
| WO | 2010116289 A1 | 10/2010 |
| WO | 2013128315 A2 | 9/2013 |
| WO | 2015001435 A1 | 1/2015 |
| WO | 2015001435 A2 | 1/2015 |

OTHER PUBLICATIONS

Heartstart Home Defibrillator Instruction Brochure, M5068A, Edition 6, 2006, 72 Page Document.
Maganis et al: "Sensor Tricorder:What Does That Sensor Know About Me?"; Hotmobile 2011, pp. 1-6.
Pohlmann: "Visible Light Communication"; Seminar Kommunikationsstandards in Der Medizintechnik, 2010, pp. 1-14.

\* cited by examiner

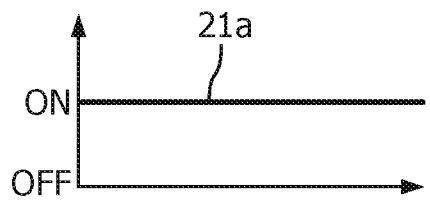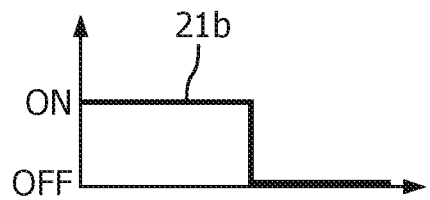
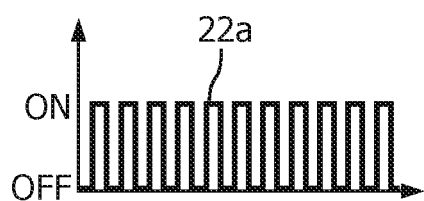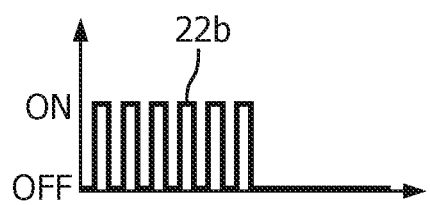
FIG. 2A					FIG. 2B
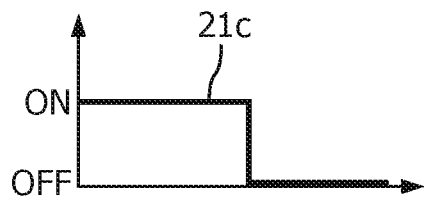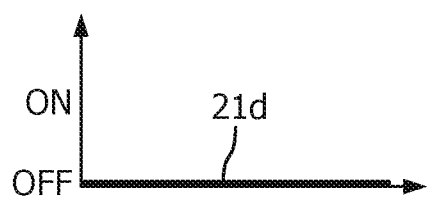
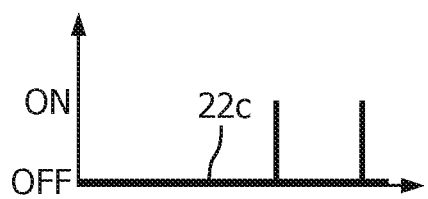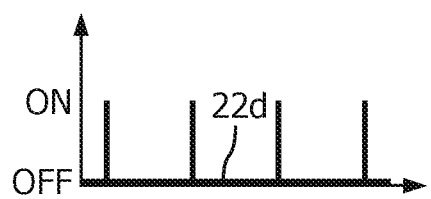
FIG. 2C					FIG. 2D

ENCODED STATUS INDICATOR FOR AUTOMATED EXTERNAL DEFIBRILLATORS

CROSS-REFERENCE TO PRIOR APPLICATIONS

This application is the U.S. National Phase application under 35 U.S.C. § 371 of International Application No. PCT/IB2015/050836, filed on Feb. 4, 2015, which claims the benefit of U.S. Provisional Patent Application No. 61/971,310, filed on Mar. 27, 2014. These applications are hereby incorporated by reference herein.

The present invention generally relates to automated external defibrillators ("AED"). The present invention specifically relates to a status indicator emitting an encoded status light including a base status of an operational readiness of the automated external defibrillator and a test status of self-test information of the automated external defibrillator.

Specifically, as known in the art, an AED may employ a ready light, for example a green light emitting diode (LED) to emit a visual indication of an operational readiness of the AED (i.e., a visual base status of the AED). For example, the ready light may be blinking to visually indicate a standby mode of the AED whereby the AED is ready for use, or may be a solid color to visually indicate that the AED is in a use mode of operation, or may be blinking in a different color and rate to visually indicate that the AED has failed a self-test and is need of attention (e.g., operational malfunction, temperature issue, improper pad cartridge installation or low battery power). The ready light may also be turned completely off to indicate a complete failure of the AED.

Additionally, as known in the art, an AED may employ an information button to access a visual indication of self-test information in detail of the AED (i.e., a visual test status of the AED). For example, the AED may flash its information button in optional conjunction with an audible indication of a need to troubleshoot the AED, whereby a pressing of the flashing information button displays detailed troubleshooting instructions and recommendations for the AED.

Other prior art AEDs utilize liquid crystal displays (LCD) to indicate a readiness status instead of LEDs. One such LCD display is taught by co-assigned U.S. Pat. No. 5,879,374 entitled "External defibrillator with automatic self-testing prior to use" and incorporated herein by reference. The AED controls such LCD displays to create a graphic, to obscure a portion of a backplane graphic, or to operate an LCD backlight in order to convey readiness information. Such an AED has a failsafe display in that a failed indication is shown on the backplane graphic even in the result of a complete loss of power.

One problem with prior art AEDs is that the readiness displays convey only limited information about the AED operational status, and only to viewers within visual range of the display. Some AEDs are arranged to transmit readiness status by alternate wireless means in parallel with the display, but such features add cost and complexity to the AED, and reduce its battery life. What is needed is a simpler means of transmitting readiness status of an AED without additional cost or power usage.

The present invention solves the prior art problem with an AED that operates to concurrently communicate basic operational readiness and self-test information of the AED in the display, as well as more detailed machine-readable status information encoded within the same display. Much more information can thus be conveyed from a single status indicator. In one embodiment, the present invention provides an intensity modulation of an encoded status light to concurrently visually indicate the base status and the test status of the AED respectively to an operator/technician and to a technician device (e.g., any type of smart handheld computer or mobile device).

One form of the present invention is an automated external defibrillator employing a self-test circuit and an encoded status indicator (e.g., an encoder and a light source preferably in the form of a light emitting diode). In operation, the self-test circuit automatically tests the automated external defibrillator and, dependent upon the outcome of the test, generates both a base status indicative of an operational readiness of the automated external defibrillator and a test status indicative of self-test information of the automated external defibrillator. The encoded status indicator concurrently visually indicates both the base status and the test status with the visual indication of the base status being perceivable to a human eye and the visual indication of the test status being in a form that is not perceivable to the human eye.

A second form of the present invention is a system employing the aforementioned automated external defibrillator and further employing a technician (e.g., a smart handheld computer or mobile device) having a light detector operable to visually detect the encoded test status information. The technician further interprets the encoded status information, displays the information, and optionally conveys the information to a remote location via a wireless transmission.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIG. 1 illustrates an exemplary embodiment of a defibrillator in accordance with the present invention.

FIGS. 2A, 2B, 2C, and 2D illustrate several exemplary forms of intensity modulation of an encoded status indicator as shown in FIG. 1.

Figure 3:
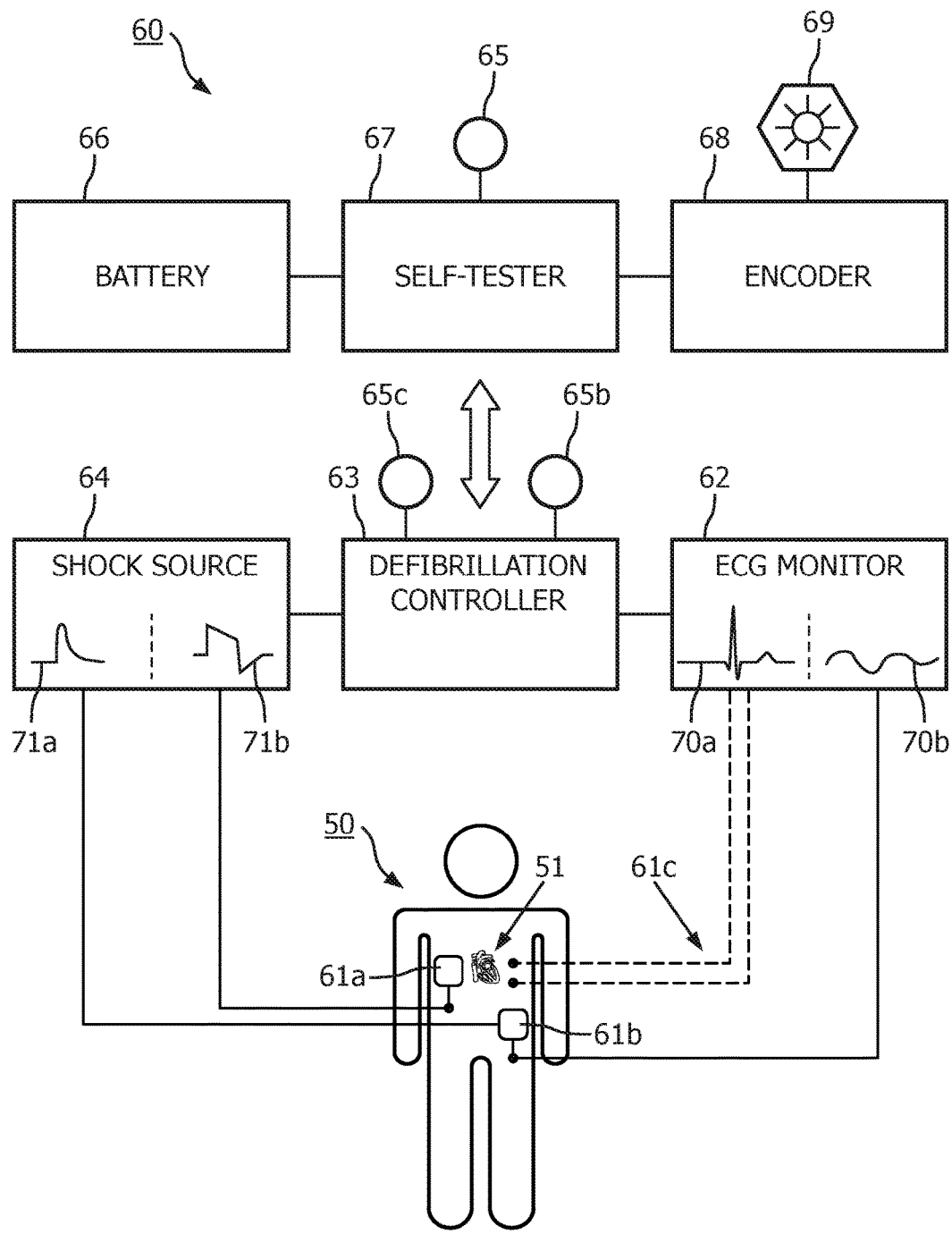

FIG. 3 illustrates an exemplary embodiment of the defibrillator shown in FIG. 1.

For purposes of the present invention, the structural terms "self-test circuit", "status indicator", "encoder", "light source", "light detector", "decoder", "display", "speaker", "electrode pad/paddle", "electrocardiogram ("ECG") monitor", "defibrillation controller", "shock source", and "battery" as well as synonymous and related terms are to be broadly interpreted as known in the art of the present invention.

To facilitate an understanding of the present invention, exemplary embodiments of the present invention will be provided herein directed to variety of intensity modulations of an encoded status indicator for concurrently visually indicating a base status and a test status of an AED.

Referring to FIG. 1, an AED 10 of the present invention comprises a self-test circuit 11 that preferably operates on an automatic and periodic basis to test critical components of the AED while it is in a standby condition. Upon completion of a self-test protocol, the self-test circuit 11 issues a base status signal 110 which indicates an operational readiness of the AED. One example of operational readiness is "ready", i.e. ready for use whereupon all critical sub-systems have passed system testing. Another example of operational readiness is "caution", i.e. can be used but should be checked, and "failure", i.e. should be removed from service for repair or maintenance. Another example of operational readiness is "failure", i.e. the AED should not be used until the failure is corrected.

Also upon completion of a self-test protocol, the self-test circuit 11 issues a test status signal 120 which indicates further self-test information of the AED (10). The self-test information is preferably more detailed information, and is also preferably related to the operational readiness information in some way. For example, the self-test information that is issued with a "ready" operational status signal could be routine data concerning past use, such as the elapsed time in days since the AED was last handled, e.g. when an AED button was last pressed, or when the electrodes or battery were last replaced. Self-test information that is issued with a "caution" operational status could be issued for an environmental temperature above or below the device specification. And self-test information that is issued with a "failure" operational status could be the failure type, such as a low battery condition, and electrode pads failure, or a device system malfunction.

The self-test circuit 11 simultaneously generates both of the base status signal 110 and the test status signal 120. The signals are in turn received as data inputs by an encoder 13. Encoder 13 combines the base status and test status signals 110,120 into a single encoded status signal 130. Embodiments of the single encoded status signal 130 are described in more detail below.

AED 10 further comprises an encoded status indicator which visually displays the single encoded status signal 130. In the FIG. 1 embodiment, the encoded status indicator includes a light source 14, such as a light emitting diode (LED). The encoder or the encoded status indicator modulates the intensity of light source 14 in a pattern that is a function of, and indicative of, the single encoded status signal. The single encoded status signal comprises two portions. A first portion is a visual indication 21 of the base status signal 110 indicative of the operational readiness. A second portion is a visual indication 22 of the test status signal 120 indicative of the self-test information.

Visual indication 21 is arranged in the pattern that can be perceived by an observer 40 as an operational status signal 110. Preferably, visual indication 21 appears as a blinking or flashing light in a pattern known in the art as indicating "ready", "caution", or "failure". Such blinking can also be generated from different colored LED lights in order to distinguish the operational status' more clearly.

Visual indication 22 is preferably arranged in a pattern that is optimized to convey a maximum of information within about the time of a single blink or flash of visual indication 21. In this regard, light source 15 may be modulated at a rate high enough to be imperceptible to an observer. For example, whereas visual indication 21 may be perceived easily at a pulse length of 1 millisecond, visual indication 22 may be modulated at a frequency of 50 microseconds, which is not perceptible to humans. The pattern of flashes, e.g. twenty possible events, obtainable by visual indication 22 within the 1 millisecond period of visual indication 21 may be sufficient to convey a fault code or other information related to the test status signal. If even more information is to be conveyed, visual indication 22 may be parsed among several adjacent time periods of visual indication 21.

Because the rate of visual modulation is so high, visual indication 22 is preferably arranged to be machine readable.

FIG. 1 further illustrates a technician device 30, which may be a stand-alone device or an off-the-shelf mobile smart phone or handheld computer with a software application particular to the invention. Technician device 30 includes an optical detector 31 operable to detect visual indication 22 of test status signal 120 and converts the signal into electrical form. Technician device 30 further includes a decoder 32 in communication with optical detector 31 which decodes test status signal 120 and passes an output the user. The output is preferably a display 33 to display the decoded test status signal 120. Optionally a speaker 34 may be employed to audibilize the decoded test status signal 120. Technician 30 may also be arranged to wirelessly transmit data pertaining to the test status signal 120 to a remote maintenance location.

Now referring to the FIGS. 2A through 2D, exemplary embodiments of patterns pertaining to the single encoded status signal are illustrated. In each of these embodiments, AED 10 intensity-modulates light source 14 to emit a status light 20 in a manner whereby a human-perceiveable operational status pattern is combined with a self test status pattern that is flashing at a frequency unperceivable to the eye. The high-frequency and short duration flashing pattern is arranged to be detectable by technician device 30.

FIG. 2A illustrates an embodiment wherein a visual indication of test status 22a is modulated within a solid-on state 21a of visual indication 21. In this embodiment, the pattern of test status 22a can be pre-determined to be indicative of a particular test status. The FIG. 2A embodiment can thus be modulated to provide an entire set of test status data in a single uninterrupted stream.

FIG. 2B illustrates a second example, wherein the visual indication 21 is in a blinking state 21b. In this embodiment, test status 22b as a whole provides the entire "on" cycle of the blinking state 21b of perceivable visual indication 21. Optionally, if the on-length of visual indication 21 is too short to convey all of the data of test status 22b, remaining data can be modulated onto the next flash of visual indication 21.

Although the modulated signals 22a and 22b show no particular data pattern, it is understood that patterns as known in the optical data transmission art may be employed to convey different types of information.

In a third example alternative to the second example as shown in FIG. 2C, a pattern 21c of visual indication 21 has an "on" cycle that is perceivable by the eye of the viewer 40. At the beginning of the "off" cycle of wave form 21c, pattern pulses 22c of visual indication 22 are output from light source 14 at a frequency detectable only by technician device 30. Thus, the viewer perceives only visual indication 21.

In a fourth example for an off state 21d of visual indication 21 as shown in FIG. 2D, pulses 22c of visual indication 22 are output during an "off" cycle of wave form 21c at a frequency that is detectable only by technician device 30.

Referring to FIG. 3, an AED 60 of the present invention employs a pair of electrode pads or paddles 61a and 61b, optional ECG leads 61c, a ECG monitor 62 (internal or external), a defibrillation controller 63, a shock source 64, operator buttons 65, a battery 66, a self-test circuit 67, an encoder 68 and a light source 69.

Electrode pads/paddles 61a and 61b are structurally configured as known in the art to be conductively applied to a patient 50 in an anterior-apex arrangement as shown in FIG. 3, or in an anterior-posterior arrangement (not shown). Electrode pad/paddles 61a and 61b conduct a defibrillation shock from shock source 64 to a heart 51 of patient 50 and conduct an ECG signal (not shown) representative of electrical activity of heart 51 of patient 50 to ECG monitor 62. Alternatively or concurrently, ECG leads 61c are connected to patient 50 as known in the art to conduct the ECG signal to ECG monitor 62.

ECG monitor 62 is structurally configured as known in the art for processing the ECG signal to measure the electrical activity of heart 51 of patient 50 as an indication patient 50 is experiencing an organized heartbeat condition or an unorganized heartbeat condition. An example of the ECG signal indicating an organized heartbeat condition is an ECG waveform 70a that is representative of an organized contraction of the ventricles of heart 51 of patient 50 being capable of pumping blood. An example of the ECG signal indicating an unorganized heartbeat condition is an ECG waveform 70b that is representative of a ventricular fibrillation of heart 51 of patient 50.

Shock source 64 is structurally configured as known in the art to store electric energy for delivery of a defibrillation shock 71 via electrode pads/paddles 61a and 61b to heart 51 of patient 50 as controlled by defibrillation controller 63. In practice, defibrillation shock 71 may have any waveform as known in the art. Examples of such waveforms include, but are not limited to, a monophasic sinusoidal waveform (positive sine wave) 71a and a biphasic truncated waveform 71b as shown in FIG. 3.

In one embodiment, shock source 64 employs a high voltage capacitor bank (not shown) for storing a high voltage via a high voltage charger and a power supply upon a pressing of an optional charge button 65b. Shock source 64 further employs a switching/isolation circuit (not shown) for selectively applying a specific waveform of an electric energy charge from the high voltage capacitor bank to electrode pads/paddles 61a and 61b as controlled by defibrillation controller 63.

Defibrillation controller 63 is structurally configured as known in the art to execute a manual cardioversion via a shock button 65c and/or an automatic cardioversion. In practice, defibrillation controller 63 employs hardware/circuitry (e.g., processor(s), memory, etc.) for executing a manual and/or an automatic cardioversion installed as software/firmware within defibrillation controller 63.

Disposable battery 66 is structurally configured as known in the art the charging various components of AED 60 as shown and not shown (e.g., a power supply).

Self-test circuit 67 is structurally configured as known in the art to execute operational testing of various components of AED 60, particularly electrode pads/paddles 61a and 61b, ECG leads 61c, ECG monitor 62, defibrillation controller 63, shock source 64 and battery 66.

In an optional embodiment, AED 60 includes a user-operated information button 65. Self-test circuit 67 activates the information button 65 when a self test status information is generated. The activation may be accompanied by another flashing light or an annunciator to indicate that information is available. When a user then presses the information button 65, the self-test circuit 67 audibly communicates the test status via a speaker (not shown).

Encoder 68 is structurally configured as would be appreciated by those skilled in the art to execute an intensity modulation of a status light as emitted by light source 69 (e.g., a light emitting diode) in accordance with an indication protocol of AED 60 to concurrently visually indicate the base status and test status of AED 60 as previously described herein.

Referring to FIGS. 1-3, those having ordinary skill in the art will appreciate numerous benefits of the present invention including, but not limited to, an alternative method to the use of a ready light for indicating an operational readiness of the AED and a separate information button for indicating self-test information of the AED. For example, the ready light may be encoded in accordance with the present invention to concurrently visually indicate the operational readiness and the self-test information of the AED. Such a feature eliminates the need for a separate circuit and indicator for the self-test information. And by encoding the two signals into a single signal with more "off" times, the invention provides for a lower duty cycle. Thus, the indicator is more power efficient, and extends battery life.

Also, in practice, those having ordinary skill in the art will appreciate a frequency range of the encoded status light perceivable to the human eye and a higher frequency range of the encoded status light unperceivable to the human eye.

In addition, it is understood that the encoded status indicator may employ a liquid crystal display (LCD) instead of an LED. In this embodiment, the LCD may be operated in a pattern which conveys similar test signal information at a frequency higher than that perceptible by the viewer, but perceptible to a technician device 30. The LCD pattern(s) may also be placed into the LCD backlight instead of into the LCD shutter.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:
1. An automated external defibrillator, comprising:
a self-test circuit operable to automatically and periodically test the automated external defibrillator and further operable to generate both a base status signal indicative of an operational readiness of the automated external defibrillator and a test status signal indicative of self-test information of the automated external defibrillator;
an encoder operably connected to the self-test circuit and operable to combine the base status signal and the test status signal into a single encoded status signal; and
an encoded status indicator in communication with the encoder, operable to visually display the single encoded status signal,
wherein the portion of the displayed single encoded status signal representing the base status signal is arranged to be human perceivable, and
wherein the portion of the displayed single encoded status signal representing the test status signal is arranged to be machine readable and to be human unperceivable, wherein the test status signal portion of the displayed single encoded status signal is modulated with a pulse length of fifty (50) microseconds.
2. The automated external defibrillator of claim 1, wherein the encoded status indicator includes:
a light source for emitting a status light, wherein the encoder controls the light source to intensity-modulate the status light as emitted by the light source as a function of the single encoded status signal.

3. The automated external defibrillator of claim 2, wherein the light source is a light emitting diode.

4. The automated external defibrillator of claim 1, wherein the self-test information in the test status signal is related to the operational readiness of the base status signal.

5. The automated external defibrillator of claim 4, wherein the operational readiness is a failure status and the self-test information consists of one of a low battery failure, and electrode pads failure and a device malfunction failure.

6. The automated external defibrillator of claim 4, wherein the operational readiness is a caution status and the self-test information is a low temperature condition.

7. The automated external defibrillator of claim 4, wherein the operational readiness is a ready status and the self-test information consists of one of an elapsed time since a last sensed button press and an elapsed time since a last electrode pads installation.

8. The automated external defibrillator of claim 1, further comprising:
a user-operated information button,
wherein the self-test circuit audibly communicates the test status in response to an actuation of the user-operated information button.

9. A display for indicating the readiness status of an automated defibrillator (AED), comprising:
First and second data inputs relating to respective operational readiness and self-test status of the AED;
an encoder operable to create a single encoded status signal from the first and second data inputs; and
a visual display of the encoded status signal which comprises a flashing light that is modulated in a pattern indicative of both the operational readiness and the self-test status of the AED, wherein the pattern portion indicative of the self-test status is at a frequency higher than that perceptible by a human viewer, wherein the pattern portion indicative of the self-test status further comprises a pulse length of fifty (50) microseconds.

10. The display of claim 9, wherein the encoded status signal comprises a self-test status pattern that is output in sequence with an operational readiness pattern.

11. The display of claim 9, wherein the encoded status signal comprises a self-test status pattern that is output simultaneously with an operational readiness pattern.

12. A system, comprising:
an automated external defibrillator including
a self-test circuit for automatically testing the automated external defibrillator and operable to generate a base status signal indicative of an operational readiness of the automated external defibrillator and a test status signal indicative of self-test information of the automated external defibrillator, and
an encoded status indicator in communication with the self-test circuit for concurrently displaying a visual indication of both the base status signal and the test status signal,
wherein the visual indication of the base status signal is perceivable to a human eye, and
wherein the visual indication of the test status signal is unperceivable to the human eye; and
a technician device including
an optical detector operable to detect the visual indication of the test status signal,
wherein the encoded status indicator is disposed to generate the visual indication of the test status signal with a pulse length of about fifty (50) microseconds.

13. The system of claim 12, wherein the technician device further includes:
a decoder in communication with the optical detector to decode the test status signal.

14. The system of claim 13, wherein the technician device further includes:
a display in communication with the decoder to visually display the decoded test status signal.

15. The system of claim 13, wherein the technician device further includes:
a speaker in communication with the decoder to audibly communicate the decoded test status signal.

16. A method for displaying the status of an automated external defibrillator, the method comprising:
providing a self-test circuit in the automated external defibrillator;
automatically producing both a base status signal indicative of an operational readiness of the automated external defibrillator and a test status signal indicative of self-test information of the automated external defibrillator; and
operating an encoded status indicator of the automated external defibrillator to concurrently visually indicate both the base status signal and the test status signal on a single display,
wherein the visual indication of the base status is perceivable to a human eye, and
wherein the visual indication of the test status is unperceivable to the human eye, wherein the encoded status indicator is disposed to generate the visual indication of the test status signal with a pulse length of fifty (50) microseconds.

17. The method of claim 16, further comprising:
activating a user-operated information button; and
audibly indicating the self-test information responsive to the activating step.

* * * * *